United States Patent [19]

Simon et al.

[11] Patent Number: 5,434,048
[45] Date of Patent: Jul. 18, 1995

[54] DNA PROBES FOR THE DETECTION OF ARBUSCULAR ENDOMYCORRHIZAL FUNGI

[75] Inventors: Luc Simon, Cap Rouge; Maurice Lalonde, St-Jean-Chrysostome, both of Canada

[73] Assignee: Universite Laval, Quebec, Canada

[21] Appl. No.: 93,144

[22] Filed: Jul. 19, 1993

Related U.S. Application Data

[63] Continuation of Ser. No. 745,192, Aug. 15, 1991, abandoned.

[51] Int. Cl.⁶ .......................... C12Q 1/68; C12P 19/34; C07H 21/04
[52] U.S. Cl. ........................................ 435/6; 435/91.2; 536/24.32; 536/24.33; 935/8; 935/77; 935/78
[58] Field of Search ............... 435/6, 91.2; 536/23.74, 536/24.32, 24.33; 935/77, 78, 8

[56] References Cited

PUBLICATIONS

Barry et al Biotechnology (1990) 8:233–236.
White et al. 1990 PCR Protocols: A Guide to Methods and Applications, Academic Press, San Diego, pp. 315–322.
Cummings et al. Gene Anal Techn (1989) 6:89–92.
Miyada, C. et al. "Oligonucleotide Hybridization Techniques." In: Methods In Enzymology (Wu, R., Editor) (1987) Academic Press, Inc., San Diego, Calif., pp. 94–107.

*Primary Examiner*—Margaret Parr
*Assistant Examiner*—Carla Myers
*Attorney, Agent, or Firm*—Cushman, Darby & Cushman

[57] ABSTRACT

The present invention relates to oligonucleotide probes useful for determining the presence in a sample of arbuscular endomycorrhizal fungi. These probes are derived from nuclear genes coding for ribosomal RNA of arbuscular endomycorrhizal fungi.

20 Claims, 4 Drawing Sheets

```
                              1
Glomus vesiculiferum      TTATAATTTA  TTTGATAGTA  C-CTTACTAC  TTGGATAACC  GTGGTNNNTC
Glomus intraradices       ..........  ..........  .AA.......  ..........  .....AAT..
Gigaspora margarita       ......G...  ..........  .CT.......  ..........  .....AAT..
Endogone pisiformis       ......G...  .......A..  ..........  ..........  .....AAT..

51
Glomus vesiculiferum      TAGAGCTAAT  ACATGCTAAA  AGCCTCCGAC  TTCTGGAAGG  GGGTGTATTT
Glomus intraradices       ..........  ..........  .-........  .........-  ..........
Gigaspora margarita       ..........  ..........  .AT.-.....  .........-  ...A......
Endogone pisiformis       ..........  ..........  .AT.-.....  .........-  ...A......

101
Glomus vesiculiferum      ATTAGATAAA  AAACCAATAT  CGGGCAACCG  ATTCCCTTGG  TGATTCATAA
Glomus intraradices       .-........  ..........  .TT-.--GG.  T.........  ..........
Gigaspora margarita       ..........  ......A...  ..........  .C..ATC...  ........G.
Endogone pisiformis       ..........  .....CG...  -.........  ..........  ..........

151
Glomus vesiculiferum      TAACTTTTCG  AATCGTAYGR  CTTTACGTCG  ACGATGAATC  ATTCAAATTT
Glomus intraradices       ..........  .....T.A..  .C..GT.CT.  .......T..  ..........
Gigaspora margarita       ..........  .....T.G..  .C..AGT.C.  .......T..  ..........
Endogone pisiformis       ..........  .....T.G..  ..........  ..........  ..........

201
Glomus vesiculiferum      CTGCCCTATC  AACTTTCGAT  GGTAGGATAG  AGGCCTACCA  TGGTGGTAAC
Glomus intraradices       ..........  ..........  ..........  ..........  ..........
Gigaspora margarita       ..........  ..........  ..........  ..........  .....TT...
Endogone pisiformis       ..........  ..........  ..........  ..........  ....AT.T..
```

Fig. 3a.

Legend:
   -   gap
   .   Same as Glomus vesiculiferum

```
                        251                                                                    300
Glomus vesiculiferum    GGGTAACGGG GTGTTAGGGC ACGACACCGG AGAGGGAGCC TGAGAAACGG
Glomus intraradices     .......... .AA......T T...TT.... .......... ..........
Gigaspora margarita     .......... .AA......T T...TT.... .......... ..........
Endogone pisiformis     .......... .......... .......... .......... ..........

301                                                                    350
Glomus vesiculiferum    CTACCACATC CAAGGATGGC AGCAGGGCGC CAAATTACCC AATCCCGACA
Glomus intraradices     .......... .....A.... .......... .......... ....T..T..
Gigaspora margarita     .......... ......A... .......... .......... ....T..T..
Endogone pisiformis     .......... .......... .......... .......... ....-..T..

351                                                                    400
Glomus vesiculiferum    CGGGGAGGTA GT-ACAATAA ATAACAATAC GGGGTTCTTT AGGATCTCGT
Glomus intraradices     .......... ..G....... .......... A..C....A .......... 
Gigaspora margarita     .......... .G........ .......... A..C....A T..G..T..
Endogone pisiformis     .......... ..G....... .......... A..CCT.... T..G..T..

401              449
Glomus vesiculiferum    ANNNGGAATG AGTACAATTT AAATCTCTTA ACGAGGAACA ATTGGAGGG
Glomus intraradices     .ATT...... .......... .......... .......... .........
Gigaspora margarita     .ATT...... .......... .....C.... .......... .........
Endogone pisiformis     .ATT...... .......... .......... .......... .........
```

Fig. 3b.

Legend:
  — : gap
  . : Same as Glomus vesiculiferum

DNA PROBES FOR THE DETECTION OF ARBUSCULAR ENDOMYCORRHIZAL FUNGI

This is a continuation of application Ser. No. 07/745,192, filed on Aug. 15, 1991.

BACKGROUND OF THE INVENTION

Many symbioses have evolved between vascular plants and soil microorganisms which result in plants having an improved acquisition of mineral nutrients, improved growth and survival. Of these symbioses, the arbuscular endomycorrhizal fungi are certainly the most ubiquitous.

Arbuscular endomycorrhizal fungi were thought to be solely of vesicular type and were referred to as "VAM fungi". Although, the expression "VAM fungi" is still used it is no longer intended to be restricted to vesicular arbuscular endomycorrhizal fungi, since arbuscular endomycorrhizal fungi are known that do not form vesicles.

A better knowledge of these symbiotic organisms might have important economic benefits since they can associate with many important crop plants. Unfortunately, these fungi have never been successfully grown in culture and hence, all the fungi must be maintained as co-cultures on colonized roots. Furthermore, it is time consuming and often not feasible to only recognize, identify and quantify the arbuscular endomycorrhizal fungi in colonized roots.

It would be highly desirable to have means to rapidly detect, identify and possibly quantify the arbuscular endomycorrhizal fungi.

DNA probes have become a widely-employed technique for detecting various organisms present in low amounts in complex samples. Thus, it would be desirable to have a DNA probe specific for the detection of the arbuscular endomycorrhizal fungi.

SUMMARY OF THE INVENTION

Surprisingly and in accordance with the present invention, there is provided novel deoxyribonucleotide probes specific for arbuscular endomycorrhizal fungi, said probes being an oligonucleotide unique to arbuscular endomycorrhizal fungi, a deoxyribonucleotide probe consisting of at least a part of isolated, purified and sequenced DNA fragment obtained by a polymerase chain reaction using the nucleic acids of these arbuscular endomycorrhizal fungi as a template and the above oligonucleotide as a primer for initiating this polymerase chain reaction, or a deoxyribonucleotide probe which sequence is identical to at least a part of the above-mentioned DNA fragment. The oligonucleotide has the following sequence: 5' GTCTAGTATAATCGTTATACAGG 3' (SEQ ID NO 1) or has the complementary sequence thereof (SEQ ID NO 2). All these probes consist of these oligonucleotides and deoxyribonucleotides labelled by any suitable means which are known in the art and which include analogues of bases.

In one object of the present invention, there is provided a method for determining the presence in a sample of any arbuscular endomycorrhizal fungi which contain genes whose nucleotide sequence is such that nucleic acids from that sample can hybridize with the oligonucleotide probe of the present invention, which comprises:

a) contacting said sample or nucleic acids extracted from said sample with an oligonucleotide probe in accordance with the present invention; and b) detecting the presence of any nucleic acid sequence or fragments thereof hybridized with said oligonucleotide probe.

A particular object of the present invention is to use the first oligonucleotide sequence (SEQ ID NO:1) in a polymerase chain reaction (PCR) assay that enables the specific amplification of a portion of the arbuscular endomycorrhizal fungi small ribosomal subunit RNA (SSU) directly from a mixture of host and fungal tissue.

These and other objects of the present invention are also achieved by the novel deoxyribonucleotide probes of the present invention.

Other advantages of the present invention will be readily illustrated by referring to the following description.

BRIEF DESCRIPTION OF THE DRAWINGS

FIGS. 3A and 3b represent the comparison of the sequences from a 449 bp fragment of the SSU of *Glomus vesiculiferum* (SEQ ID NO:3), *Glomus intraradices* (SEQ ID NO:4), *Gigaspora margarita* (SEQ ID NO:5) and *Endogone pisiformis* (SEQ ID NO:6).

DETAILED DESCRIPTION OF THE INVENTION

Figure 1:
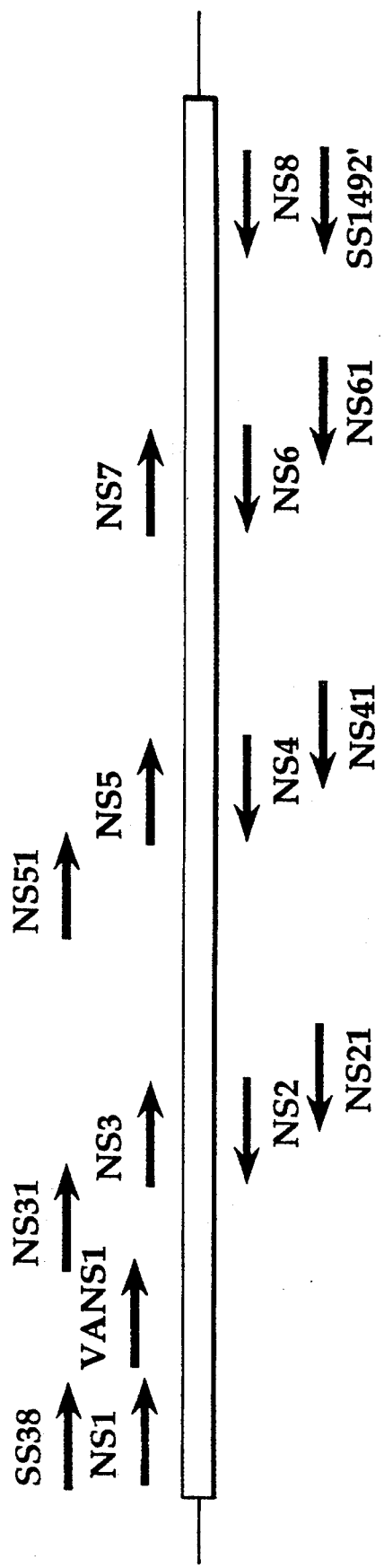
FIG. 1 is schematic representation of the location of the universal primers and taxon specific oligonucleotide of the present invention (VANS1) (SEQ ID NO:1).

The 23 mer deoxyoligonucleotide of sequence, 5'GTCTAGTATAATCGTTATACAGG, VANS1 (SEQ ID NO:1), which is complementary to the nuclear genes coding for the small ribosomal subunit RNA of arbuscular endomycorrhizal fungi, was designed after comparing the sequence of this gene obtained from *Glomus intraradices* (Shenck & Smith, DAOM 197198) and *Gigaspora margarita* (Becker & Hall, DAOM 194757) with that of a non-arbuscular endomycorrhizal fungus, *Endogone pisiformis* (These cultures have been deposited at the Biosystematics Research Centre, Wm Saunders Bldg., C.E.F. Ottawa, Ontario K1A 0C6). The location on this gene of the region corresponding to this 23 mer oligonucleotide is illustrated in FIG. 1, as well as that of some other oligonucleotides whose sequences are complementary to most eukaryotic nuclear genes coding for the small ribosomal subunit RNA (universal primers).

This aforementioned oligonucleotide was then synthesized using commercially available phosphoramidite solid phase DNA synthesizer.

The specificity of the oligonucleotide for arbuscular endomycorrhizal fungi was experimentally established by testing it on a number of fungi and plants.

Figure 2:
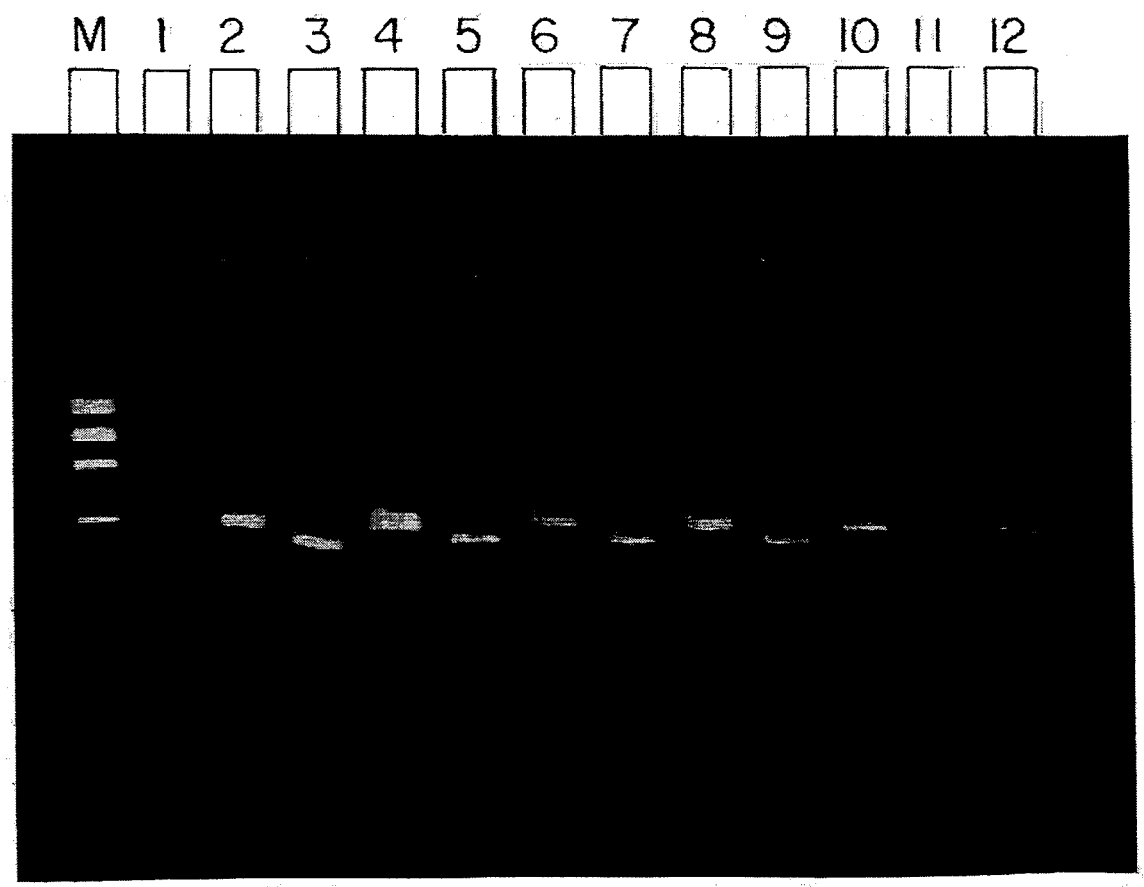
FIG. 2 represents the electrophoregram of taxon specific amplification of the nuclear genes coding for the small ribosomal subunit RNA of arbuscular endomycorrhizal fungi.

The usefulness of this oligonucleotide was further demonstrated by using it as an arbuscular endomycorrhizal fungi specific primer in polymerase chain reaction (PCR) assays (FIG. 2).

When used herein the expression "arbuscular endomycorrhizal fungi" is intended to include all the members of this type of fungi and more specifically the following fungi *Glomus mosseae, Glomus intraradices,*

*Gigaspora gigantea, Gigaspora margarita, Entrophospora colombiana* and *Scutellospora pellucida*.

The present invention will be more readily understood by referring to the following examples which are given to illustrate the invention rather that to limit its scope.

EXAMPLE I

Obtention of small ribosomal subunit RNA sequences (SSU) from arbuscular endomycorrhizal fungi; and their relatives The following procedure has been performed to obtain the gene sequence of arbuscular endomycorrhizal fungi.

Locations of the universal primers and taxon specific primer (VANS1) (SEQ ID NO:1) are shown in FIG. 1. DNAs of *Glomus intraradices* and *Gigaspora margarita* were isolated from a small number of spores (60 and 20 respectively) as described below, while DNA of *Endogone pisiformis* was isolated from mycelium grown in axenic culture by standard methods.

For Glomus and Gigaspora, since no arbuscular endomycorrhizal fungi were available in pure culture, a co-culture system was used where plant roots, following transformation by *Agrobacterium rhizogenes*, can be maintained and rapidly propagated in vitro. These root cultures were inoculated with a single surface sterilized spore of the arbuscular endomycorrhizal fungal isolate. A number of viable and axenic spores were collected after a few months of incubation.

The spores were collected with forceps, placed in a microcentrifuge tube, crushed with a miniature pestle, and 40 μL of Chelex TM resin (20% in sterile water) were added, followed by sterile water to a final of volume of 200 μL.

After four freeze-thaw cycles, the tube was centrifuged for 2 min. and the supernatant was treated with RNAse. This crude extract was diluted 1/50 and used as template for PCR. Two overlapping fragments were amplified in separate reactions using the following primer pairs: NS1/NS6 (SEQ ID NO:8/SEQ ID NO:17) and NS3/NS8 (SEQ ID NO:11/SEQ ID NO:20).

The reaction mixture consisted of template solution and a master mix (20 mM Tris-HCl pH 8.4, 100 mM KCl, 3 mM $MgCl_2$, 0.02% gelatin, 60 mM of each nucleotide (1:1 v/v) containing 0.5 unit Tag DNA polymerase and 1 pmole of two appropriate primers in 20 μL total reaction volume, overlayed with light mineral oil.

The temperature profile was programmed to repeat 40 times a cycle of denaturation (2 min. at 95° C. for the first cycle, 35 sec. at 96° C. afterward), annealing (55 sec. at 53° C.) and polymerization (35 sec. at 72° C. for the first 14 cycles, 2 min. at 72° C. for the next 11 cycles, 3 min. at 72° C. for the last 15 cycles), followed by a final extension step of 10 min. at 72° C.

These gene fragments were gel purified, diluted, and used as templates for subsequent rounds of asymmetric amplifications (MYCOLOGIA, Bruns T. D. et al., (1980), 82, pp. 175-184) using various combinations of the internal primers indicated. Sequences of the primers indicated are described in Table 1.

The single stranded DNAs produced by these asymmetric amplifications were then purified by centrifugal ultrafiltration and sequenced using commercially available DNA sequencing kits and following the recommendations of the manufacturers. The complete sequences of these arbuscular endomycorrhizal fungi, used in the present invention, can be obtained from the EMBL Data Library, Postfach 10.2209, Meyerhorstrasse 1, D-6900 Heidelberg, Germany or GenBank, Mail Stop K710, Los Alamos National Laboratory, Los Alamos, N. Mex. 87545, USA where they have been deposited under the accession numbers X58724 (EP 18S RRNA), X58725 (GI 18S RRNA) and X58726 (GM 18S RRNA).

These results demonstrate that the universal primers (listed in Table 1) can be used to obtain sequence data from arbuscular endomycorrhizal fungi. In addition to the primers already described by Bousquet et al (Reference[1], ibid page 8) and White et al (Reference[2], ibid, page 8), 5 new universal primers were designed and have proven to be useful in obtaining more complete sequences since they can be used to produce overlapping fragments of the gene coding for the samll ribosomal subunit RNA. These 5 new universal primers are not intended to be part of the present invention.

It should be stressed that the protocol used to obtain such sequences from purified spores of arbuscular endomycorrhizal fungi could not have been used with colonized roots or such type of complex sample, since the universal primers would then amplify a mixture of genes from the plants and fungi, which is not useful for sequencing. In order to be able to specifically amplify or detect the gene coding for the small ribosomal subunit RNA from arbuscular endomycorrhizal fungi, the VANS1 (SEQ ID NO:1) primer, object of the present invention, was designed and synthesized. Its specificity and usefulness will be illustrated in the following examples.

TABLE 1

| Primers for amplification of eucaryotic nuclear 18S ribosomal genes | | |
|---|---|---|
| Name | Sequence* | Reference |
| SS38 (SEQ ID NO: 7) | GTCGACTCCTGCCAGTAGTCATATGCTT | Bousquet[1] |
| NS1 (SEQ ID NO: 8) | GTAGTCATATGCTTGTCTC | White[2] |
| NS2 (SEQ ID NO: 9) | GGCTGCTGGCACCAGACTTGC | White[2] |
| NS21 (SEQ ID NO: 10) | AATATACGCTATTGGAGCTGG | 3 |
| NS3 (SEQ ID NO: 11) | GCAAGTCTGGTGCCAGCAGCC | White[2] |
| NS31 (SEQ ID NO: 12) | TTGGAGGGCAAGTCTGGTGCC | 3 |
| NS4 (SEQ ID NO: 13) | CTTCCGTCAATTCCTTTAAG | White[2] |
| NS41 (SEQ ID NO: 14) | CCCGTGTTGAGTCAAATTA | 3 |
| NS5 (SEQ ID NO: 15) | AACTTAAAGGAATTGACGGAAG | White[2] |
| NS51 (SEQ ID NO: 16) | GGGGGAGTATGGTCGCAAGGC | 3 |
| NS6 (SEQ ID NO: 17) | GCATCACAGACCTGTTATTGCCTC | White[2] |
| NS61 (SEQ ID NO: 18) | CAGTGTAGCGCGCGTGCGGC | 3 |
| NS7 (SEQ ID NO: 19) | GAGGCAATAACTGGTCTGTGATGC | White[2] |
| NS8 (SEQ ID NO: 20) | TCCGCAGGTTCACCTACGGA | White[2] |

TABLE 1-continued

| Primers for amplification of eucaryotic nuclear 18S ribosomal genes | | |
|---|---|---|
| Name | Sequence* | Reference |
| SS1492 (SEQ ID NO: 21) | GCGGCCGCTACGGMWACCTTGTTACGACTT | Bousquet[1] |

*the sequences are written 5' to 3'
[1] CAN. J. FOR. RES., Bousquet et al. (1990) 20, 254–257
[2] PCR protocols, a guide to Methods and applications, White et al., M.A. Innis et al. (ed), (1990) pp. 315–322
[3] the present patent application.

EXAMPLE II

SPECIFICITY OF VANS1

To examine the specificity of the VANS1 (SEQ ID NO:1) primer, it was paired with a downstream "universal" primer and its ability to amplify a 550 bp portion of the SSU sequences from DNAs of other endomycorrhizal fungi as well as a variety of other fungi and plants was tested. The fungi used for testing span a broad phylogenetic range and included putative relatives of endomycorrhizal fungi as well as other rhizosphere associates such as ectomycorrhizal species and root pathogens. Among the organisms tested, only endomycorrhizal fungi yielded the expected SSU fragment, while control experiments using the NS1 (SEQ ID NO:8) universal primer demonstrated that a larger overlapping region of the SSU could be amplified from all of the samples (FIG. 2 and Table 2).

In those experiments, the reaction mixture consisted of template solution and a master mix (20 mM Tris-HCl pH 8.4, 100 mM KCl, 3 mM MgCl$_2$, 0.02% gelatin, 60 mM of each nucleotide (1:1 v/v) containing 0.5 unit Taq DNA polymerase and 1 pmole of two appropriate primers in 20 μL total reaction volume, overlayed with light mineral oil.

The temperature profile was programmed to repeat 40 times a cycle of denaturation (1 min. at 95° C.), annealing (55 sec. at 55° C.) and polymerization (1 min. at 72° C. for the first 25 cycles, 2 min. at 72° C. for the next 10 cycles, 3 min. at 72° C. for the last 5 cycles), followed by a final extension step of 10 min. at 72° C.

For the experiments, the results of which are illustrated in FIG. 2, aliquots of DNA samples were amplified with universal primers, SS38/NS21 (SEQ ID NO:7/SEQ ID NO:10) (even lanes) and with the taxon-specific primer, VANS1 (SEQ ID NO:1), coupled with one of the same universal primers, NS21 (SEQ ID NO:10) (odd lanes). Note that the predicted 550 bp VAM specific product was only amplified from samples containing DNA of VAM fungi: purified SSU DNA of Gi. margarita (lanes 3,4) crude extracts of E. colombiana spores (lanes 5,6), purified SSN DNA of G. intraradices (lanes 7,8) and crude extracts from leek roots colonized by G. vesiculiferum (lanes 9,10), but the overlapping 600 bp universal product was amplified from all samples including: the purified SSU DNA of the non-VAM fungus Endogone pisiformis (lanes 1,2), and Alnus crispa total genomic DNA (lanes 11,12). Lane M is ΦX174/HaeIII size marker.

These results demonstrate that DNAs from all these samples can be amplified with the universal primers, but that only arbuscular endomycorrhizal fungi DNA was amplified when the VANS1 primer was used.

Such experiments were performed with a broader range of plants and fungi and the results are summarized in Table 2. There can be observed that the VANS1 (SEQ ID NO:1) probe of the present invention demonstrates a specificity to the arbuscular endomyccorhizal fungi (Glomus mosseae, Glomus intraradices, Gigaspora gigantea, Gigaspora margarita, Entrophospora colombiana & Scutellospora pellucida) whereas the universal primers (NS1/NS2 (SEQ ID NO:8/SEQ ID NO:9) or SS38/NS21) (SEQ ID NO:7/SEQ ID NO:10) again can amplify all samples tested.

The general applicability of this primer for all endomycorrhizal fungi is suggested by the finding that the amplification succeeded not only with other species of Glomus and Gigaspora, but also with species from two other genera: Entrophospora and Scutellospora. VANS1 (SEQ ID NO:1) has been found to pair with other universal primers (e.g. NS8 or SS1492) (SEQ ID NO:20 or SEQ ID NO:21) which yield virtually full length SSU genes from these species.

TABLE 2

Assessment of the specificity of VANS1 vs universal primers for the amplification of a portion of the eukaryotic SSU

| Source of DNA | NS1 primer | VANS1 primer |
|---|---|---|
| Plants | | |
| *Angiosperms* | | |
| *Allium porum* | + | − |
| *Alnus crispa* | + | − |
| *Alnus glutinosa* | + | − |
| *Arabidonsis thaliana* | + | − |
| *Quercus agrifolia* | + | − |
| *Gymnosperms* | | |
| *Ables concolor* | + | − |
| *Pinus ponderosa* | + | − |
| Fungi and Fungal-like Protists | | |
| *Oomycetes* | | |
| *Phytophtora cinnamomi* a2423 | + | − |
| *Zygomyceteus* | | |
| *Endogone visiformis* CRBF0001 | + | − |
| *Mycotypha africana* NRL2978 | + | − |
| *Phycomyces blakesleeanus* NRL1465 | + | − |
| *Syncephalastrum racemosum* NRL2496 | + | |
| *Glomus mosseae* INVAM156 | + | + |
| *Glomus intraradices* DOAM197198 | + | + |
| *Gigaspora gigantea* WV932 | + | + |
| *Gigaspora margarita* DOAM194757 | + | + |
| *Entrophospora colombiana* WV877 | + | + |
| *Scutellospora vellucida* WV873 | + | + |
| *Ascomycetes* | | |
| *Cenococum geophile* S166 | + | − |
| *Diplodasus geotrichium* ATCC22600 | + | − |
| *Neurospora tetrasperma* FGSC1271 | + | − |
| *Tuber melanosporum* S489 | + | − |
| *Wilcoxina mikolae* CSY4 | + | − |
| *Basidiomycetes* | | |
| *Boletus satanas* TDB1000 | + | − |
| *Dacromyces nalmatus* SR449 | + | − |
| *Peridermium harknessi* RUR152 | + | − |
| *Russula laurocerasi* TDB122 | + | − |

TABLE 2-continued

Assessment of the specificity of VANS1 vs universal primers for the amplification of a portion of the eukaryotic SSU

| Source of DNA | NS1 primer | VANS1 primer |
|---|---|---|
| *Telephora americana* S4938 | + | − |

Legend:
+: NS1/NS2 or SS38/NS21 (SEQ ID NO: 8/SEQ ID NO: 9) (SEQ ID NO: 7/SEQ ID NO: 10) primer pairs
: VANS1/NS21 (SEQ ID NO: 7/SEQ ID NO: 9) or VANS1 (SEQ ID NO: 1)/NS2 primer pairs

EXAMPLE III

USE OF COLONIZED ROOTS

Colonized leek (*Allium porum*) roots have been chosen for this test, because leek pot cultures are commonly used to maintain and produce endomycorrhizal fungi. Such colonized roots resemble field collected material, but have the advantage of containing a unique and known endomycorrhizal fungi associated.

Leek colonized with *Glomus vesiculiferum* were maintained in standard growth cabinet conditions. Their roots were harvested, and DNA extracted as described by Bousquet et al (Reference[1], ibid page 8) and used as templates for amplification with the VANS1 (SEQ ID NO:1) and NS21 (SEQ ID NO:10) primer. Briefly, the protocol has consisted in homogenizing approximatively 100 mg of fresh roots, ground in liquid nitrogen, in 750 µL of extraction buffer (100 mM Tris, 1.4M NaCl, 20 mM EDTA, 2% CTAB, 0.2% β-mercaptoethanol, pH 9.5) using a mortar and pestle. The homogenate was incubated 60 min. at 65° C. and extracted with an equal volume of chloroform. After centrifugating at 13000×g for 15 min., the aqueous phase was transferred. The DNA was precipitated with the addition of 1/10 volume 3M sodium acetate and 1 volume isopropanol. After centrifugating at 6000×g for 15 min., the DNA pellet was vacuum dried and resolubilised in 100 µL of water.

The expected 550 bases fragment was obtained (FIG. 2) and directly sequenced. A simple alignment with other corresponding sequences confirms that this specifically amplified fragment belongs to a Glomus SSU (FIGS. 3a and 3b). The fragment differed from the *Glomus intraradices* gene only at 3 positions out of 447 sequenced, while *Gigaspora margarita* and *Endogone pisiformis* exhibited 45 and 46 differences respectively. So these results confirm that using the VANS1 (SEQ ID NO:1) primer, ribosomal genes from arbuscular endomycorrhizal fungi can be specifically amplified and sequenced directly from colonized roots.

The present invention thus provides specific and sensitive DNA probes, and a method for the detection of arbuscular endomycorrhizal fungi in root sample.

Alternatively, the present invention can be used to provide RNA probes specific for arbuscular endomycorrhizal fungi. The present invention may also be used to provide ribosomal DNA probes that are specific for individual arbuscular endomycorrhizal fungi and which enable the amplification of the genes of these individual fungi.

Although the present invention has been described in detail by reference to certain specific examples of deoxyribonucleotide probes and *Glomus intraradices* and *Gigaspora margarita* species, it should be apparent to one skilled in the art that various modifications are possible and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

---

What is claimed is:

1. An oligonucleotide probe specific for arbuscular endomycorrhizal fungi which has a nucleic acid sequence selected from the group consisting of:

5'GTCTAGTATAATCGTTATACAGG 3' (SEQ ID NO: 1), and
5'CCTGTATAACGATTATACTAGAC 3' (SEQ ID NO: 2).

2. The oligonucleotide probe according to claim 1 wherein the arbuscular endomycorrhizal fungi include all the following species: *Glomus mosseae, Glomus intraradices, Glomus vesiculiferum, Gigaspora gigantea, Gigaspora margarita, Entrophorspora colombiana* and *Scutellospora pellucida.*

3. A method for determining the presence in a sample of any arbuscular endomycorrhizal fungi which contains nucleic acids whose nucleotide sequence is such that said nucleic acids hybridize with the oligonucleotide of claim 1, which comprises:

a) extracting said nucleic acids from said sample and contacting same with the oligonucleotide of claim 1; and b) detecting the presence of any nucleic acids, hybridized with said oligonucleotide as an indication of the presence of arbuscular endomycorrhizal fungi.

4. A method of making a deoxyribonucleotide probe specific to one single species of arbuscular endomycorrhizal fungi, comprising the steps of:

amplifying a DNA fragment by a polymerase chain reaction using nucleic acids of said arbuscular endomycorrhizal fungi as a template and the oligonucleotide of claim 1 as a primer for initiating said polymerase chain reaction;

isolating and purifying said DNA fragment;

sequencing said DNA fragment;

synthesizing a nucleic acid which consists of a part of said DNA fragment, said part having a nucleic acid sequence which is unique and specific to one species of arbuscular endomycorrhizal fungi; and labelling said nucleic acid in order to obtain said probe.

5. A method of making a deoxyribonucleotide probe specific to more than one species of arbuscular endomycorrhizal fungi, comprising the steps of:
amplifying a DNA fragment by a polymerase chain reaction using nucleic acids of said arbuscular endomycorrhizal fungi as a template and the oligonucleotide of claim 1 as a primer for initiating said polymerase chain reaction;
isolating and purifying said DNA fragment;
sequencing said DNA fragment;
synthesizing a nucleic acid which consists of a part of said DNA fragment, said part having a nucleic acid sequence which is common and specific to said more than one species of arbuscular endomycorrhizal fungi; and
labelling said nucleic acid in order to obtain said probe.

6. A method for determining the presence in a sample of any arbuscular endomycorrhizal fungi which contains nucleic acids whose nucleotide sequence is such that said nucleic acids hybridize with the oligonucleotide of claim 1, which comprises:
a) amplifying a DNA fragment by a polymerase chain reaction using nucleic acids of said sample as a template, the oligonucleotide of claim 1 as a first primer for initiating said polymerase chain reaction and a second primer which is optionally paired with said first primer for initiating said polymerase chain reaction, said second primer being a universal primer that is complementary to the DNA sequence encoding the eukaryotic small ribosomal sub-unit RNA; and
b) detecting the resulting amplified DNA fragment as an indication of the presence of arbuscular endomycorrhizal fungi.

7. A method for determining a portion of the DNA sequence of any arbuscular endomycorrhizal fungi which contain nucleic acids whose nucleotide sequence is such that said nucleic acids hybridize with the oligonucleotide of claim 1, which comprises:
a) amplifying a DNA fragment by a polymerase chain reaction using nucleic acids of said sample as a template, the oligonucleotide of claim 1 as a first primer for initiating said polymerase chain reaction and a second primer which is optionally paired with said first primer for initiating said polymerase chain reaction, said second primer being a universal primer that is complementary to the DNA sequence encoding the eukaryotic small ribosomal sub-unit RNA;
b) detecting the presence of the expected amplified DNA fragment after said polymerase chain reaction; and
c) sequencing said amplified DNA fragment.

8. A method according to claim 6 wherein said second primer is selected form the group consisting of the following oligonucleotides:

| | | | |
|---|---|---|---|
| GTCGACTCCT | GCCAGTAGTC | ATATGCTT | SEQ ID NO: 7 |
| GTAGTCATAT | GCTTGTCTC | | SEQ ID NO: 8 |
| GGCTGCTGGC | ACCAGACTTG | C | SEQ ID NO: 9 |
| AATATACGCT | ATTGGAGCTG | G | SEQ ID NO: 10 |
| CTTCCGTCAA | TTCCTTTAAG | | SEQ ID NO: 13 |
| CCCGTGTTGA | GTCAAATTA | | SEQ ID NO: 14 |
| GCATCACAGA | CCTGTTATTG | CCTC | SEQ ID NO: 17 |
| CAGTGTAGCG | CGCGTGCGGC | | SEQ ID NO: 18 |
| TCCGCAGGTT | CACCTACGGA | | SEQ ID NO: 20, and |
| GCGGCCGCTA | CGGACCTTGT | TACGACTT | SEQ ID NO: 21. | primer for initiating said polymerase chain reaction and a second primer which is optionally paired with said first primer for initiating said polymerase chain reaction, said second primer being a universal primer that is complementary to the DNA sequence 9. A method according to claim 7 wherein said second primer is selected from the group consisting of the following oligonucleotides:

| | | | |
|---|---|---|---|
| GTCGACTCCT | GCCAGTAGTC | ATATGCTT | SEQ ID NO: 7 |
| GTAGTCATAT | GCTTGTCTC | | SEQ ID NO: 8 |
| GGCTGCTGGC | ACCAGACTTG | C | SEQ ID NO: 9 |
| AATATACGCT | ATTGGAGCTG | G | SEQ ID NO: 10 |
| CTTCCGTCAA | TTCCTTTAAG | | SEQ ID NO: 13 |
| CCCGTGTTGA | GTCAAATTA | | SEQ ID NO: 14 |
| GCATCACAGA | CCTGTTATTG | CCTC | SEQ ID NO: 17 |
| CAGTGTAGCG | CGCGTGCGGC | | SEQ ID NO: 18 |
| TCCGCAGGTT | CACCTACGGA | | SEQ ID NO: 20, and |
| GCGGCCGCTA | CGGACCTTGT | TACGACTT | SEQ ID NO: 21. |

10. A method according to claim 4 wherein said DNA fragment has a nucleotide sequence which is selected from the group consisting of the following nucleotide sequences:

| | | | | |
|---|---|---|---|---|
| TTATAATTTA | TTTGATAGTA | CCTTACTACT | TGGATAACCG | TGGTAATTCT |
| AGAGCTAATA | CATGCTAAAA | CCTCCGACTT | CTGGAAGGGG | GTGTATTTAT |
| TAGATAAAAA | ACCAATATCG | GGCAACCGAT | TCCCTTGGTG | ATTCATAATA |
| ACTTTTCGAA | TCGTATGRCT | TTACGTCGAC | GATGAATCAT | TCAAATTTCT |
| GCCCTATCAA | CTTTCGATGG | TAGGATAGAG | GCCTACCATG | GTGGTAACGG |
| GTAACGGGGT | GTTAGGGCAC | GACACCGGAG | AGGGAGCCTG | AGAAACGGCT |
| ACCACATCCA | AGGATGGCAG | CAGGCGCGCA | AATTACCCAA | TCCCGACACG |
| GGGAGGTAGT | GACAATAAAT | AACAATACGG | GGTTCTTTAG | GATCTCGTAA |
| TTGAATGAG | TACAATTTAA | ATCTCTTAAC | GAGGAACAAT | TGGAGGG |
| | | | | (SEQ ID NO: 3), |
| TTATAATTTA | TTTGATAGTA | CCTTACTACT | TGGATAACCG | TGGTAATTCT |
| AGAGCTAATA | CATGCTAAAA | CCTCCGACTT | CTGGAAGGGG | GTGTATTTAT |

-continued

| | | | | |
|---|---|---|---|---|
| TAGATAAAAA | ACCAATATCG | GGCAACCGAT | TCCCTTGGTG | ATTCATAATA |
| ACTTTTCGAA | TCGTATGACT | TTACGTCGAC | GATGAATCAT | TCAAATTTCT |
| GCCCTATCAA | CTTTCGATGG | TAGGATAGAG | GCCTACCATG | GTGGTAACGG |
| GTAACGGGGT | GTTAGGGCAC | GACACCGGAG | AGGGAGCCTG | AGAAACGGCT |
| ACCACATCCA | AGGATGGCAG | CAGGCGCGCA | AATTACCCAA | TCCCGACACG |
| GGGAGGTAGT | GACAATAAAT | AACAATACGG | GGTTCTTTAG | GATCTCGTAA |
| TTGGAATGAG | TACAATTTAA | ATCTCTTAAC | GAGGAACAAT | TGGAGGG |
| | | | | (SEQ ID NO: 4), and |
| TTATAGTTTA | TTTGATAGTA | CAATTACTAC | TTGGATAACC | GTGGTAATTC |
| TAGAGCTAAT | ACATGCTAAA | AATCCCGACT | TCTGGAAGGG | ATGTATTTAT |
| TAGATAAAAA | CCAATAACCT | TCGGGTTTCC | CTTGGTGATT | CATGATAACT |
| TTTCGAATCG | TATGGCCTTG | TGCTGACGAT | GTATCATTCA | AATTTCTGCC |
| CTATCAACTT | TCGATGGTAG | GATAGAGGCC | TACCATGGTT | TTAACGGGTA |
| ACGGGGAATT | AGGGTTCGAT | TCCGGAGAGG | GAGCCTGAGA | AACGGCTACC |
| ACATCCAAGG | AAGGCAGCAG | GCGCGCAAAT | TACCCAATCC | CGATACGGGG |
| AGGTAGTGAC | AATAAATAAC | AATACAGGGC | TCTTATGGGT | CTTGTAATTG |
| GAATGAGTAC | AATTTAAATC | TCTTAACGAG | GAACAATTGG | AGGG |
| | | | | (SEQ ID NO: 5) | and wherein the nucleotide sequence of SEQ ID NO: 3 is obtained by amplifying the nucleic acids of *Glomus vesiculiferm*, the nucleotide sequence of SEQ ID NO: 4 is obtained by amplifying the nucleic acids of *Glomus intraradices*, and the nucleotide sequence of SEQ ID NO: 5 is obtained by amplifying the nucleic acids of *Gigaspora margarita*.

11. A method according to claim 5 wherein said DNA fragment has a nucleotide sequence which is selected from the group consisting of the following nucleotide sequences:

| | | | | |
|---|---|---|---|---|
| TTATAATTTA | TTTGATAGTA | CCTTACTACT | TGGATAACCG | TGGTAATTCT |
| AGAGCTAATA | CATGCTAAAA | CCTCCGACTT | CTGGAAGGGG | GTGTATTTAT |
| TAGATAAAAA | ACCAATATCG | GGCAACCGAT | TCCCTTGGTG | ATTCATAATA |
| ACTTTTCGAA | TCGTATGRCT | TTACGTCGAC | GATGAATCAT | TCAAATTTCT |
| GCCCTATCAA | CTTTCGATGG | TAGGATAGAG | GCCTACCATG | GTGGTAACGG |
| GTAACGGGGT | GTTAGGGCAC | GACACCGGAG | AGGGAGCCTG | AGAAACGGCT |
| ACCACATCCA | AGGATGGCAG | CAGGCGCGCA | AATTACCCAA | TCCCGACACG |
| GGGAGGTAGT | GACAATAAAT | AACAATACGG | GGTTCTTTAG | GATCTCGTAA |
| TTGGAATGAG | TACAATTTAA | ATCTCTTAAC | GAGGAACAAT | TGGAGGG |
| | | | | (SEQ ID NO: 3), |
| TTATAATTTA | TTTGATAGTA | CCTTACTACT | TGGATAACCG | TGGTAATTCT |
| AGAGCTAATA | CATGCTAAAA | CCTCCGACTT | CTGGAAGGGG | GTGTATTTAT |
| TAGATAAAAA | ACCAATATCG | GGCAACCGAT | TCCCTTGGTG | ATTCATAATA |
| ACTTTTCGAA | TCGTATGACT | TTACGTCGAC | GATGAATCAT | TCAAATTTCT |
| GCCCTATCAA | CTTTCGATGG | TAGGATAGAG | GCCTACCATG | GTGGTAACGG |
| GTAACGGGGT | GTTAGGGGCAC | GACACCGGAG | AGGGAGCCTG | AGAAACGGCT |
| ACCACATCCA | AGGATGGCAG | CAGGCGCGCA | AATTACCCAA | TCCCGACACG |
| GGGAGGTAGT | GACAATAAAT | AACAATACGG | GGTTCTTTAG | GATCTCGTAA |
| TTGGAATGAC | TACAATTTAA | ATCTCTTAAC | GAGGAACAAT | TGGAGGG |
| | | | | (SEQ ID NO: 4), and |
| TTATAGTTTA | TTTGATAGTA | CAATTACTAC | TTGGATAACC | GTGGTAATTC |
| TAGAGCTAAT | ACATGCTAAA | AATCCCGACT | TCTGGAAGGG | ATGTATTTAT |
| TAGATAAAAA | CCAATAACCT | TCGGGTTTCC | CTTGGTGATT | CATGATAACT |
| TTTCGAATCG | TATGGCCTTG | TGCTGACGAT | GTATCATTCA | AATTTCTGCC |
| CTATCAACTT | TCGATGGTAG | GATAGAGGCC | TACCATGGTT | TTAACGGGTA |
| ACGGGGAATT | AGGGTTCGAT | TCCGGAGAGG | GAGCCTGAGA | AACGGCTACC |
| ACATCCAAGG | AAGGCAGCAG | GCGCGCAAAT | TACCCAATCC | GCATACGGGG |
| AGGTAGTGAC | AATAAATAAC | AATACAGGGC | TCTTATGGGT | CTTGTAATTG |
| GAATGAGTAC | AATTTAAATC | TCTTAACGAG | GAACAATTGG | AGGG |
| | | | | (SEQ ID NO: 5) | and wherein the nucleotide sequence of SEQ ID NO: 3 is obtained by amplifying the nucleic acids of *Glomus vesiculiferm*, the nucleotide sequence of SEQ ID NO: 4 is obtained by amplifying the nucleic acids of *Glomus intraradices*, and the nucleotide sequence of SEQ ID NO: 5 is obtained by amplifying the nucleic acids of *Gigaspora margarita*.

12. A probe specific to one species of arbuscular endomycorrhizal fungi made by the process of claim 4.

13. A probe specific to more than one species of arbuscular endomycorrhizal fungi made by the process of claim 5.

14. A probe specific to one species of arbuscular endomycorrhizal fungi made by the process of claim 10.

15. A probe specific to more than one species of arbuscular endomycorrhizal fungi made by the process of claim 11.

16. A method for determining the presence in a sample of one species of arbuscular endomycorrhizal fungi which contains nucleic acids whose nucleotide sequence is such that said nucleic acids hybridize with the probe of claim 12, which comprises:

a) extracting said nucleic acids from said sample and contacting same with the probe of claim 12, and b) detecting the presence of any nucleic acids hybridized with said probe as an indication of the presence of said species of arbuscular endomycorrhizal fungi.

17. A method of determining the presence in a sample of at least one species of arbuscular endomycorrhizal fungi which contain nucleic acids whose nucleotide sequence is such that said nucleic acids hybridize with the probe of claim 13, which comprises:

a) extracting said nucleic acids from said sample and contacting same with the probe of claim 13; and b) detecting the presence of any nucleic acids hybridized with said probe as an indication of the presence of arbuscular endomycorrhizal fungi.

18. A method for determining the presence in a sample of one species of arbuscular endomycorrhizal fungi which contains nucleic acids whose nucleotide sequence is such that said nucleic acids hybridize with the probe of claim 14, which comprises:
   a) extracting said nucleic acids from said sample and contacting same with the probe of claim 14, and
   b) detecting the presence of any nucleic acids hybridized with said probe as an indication of the presence of said single species of arbuscular endomycorrhizal fungi.

19. A method for determining the presence in a sample of at least one species of arbuscular endomycorrhizal fungi which contain nucleic acids whose nucleotide sequence is such that said nucleic acids hybridize with the probe of claim 15, which comprises:
   a) extracting said nucleic acids from said sample and contacting same with the probe of claim 15; and
   b) detecting the presence of any nucleic acids hybridized with said probe as an indication of the presence of arbuscular endomycorrhizal fungi.

20. A method according to anyone of claims 3, 4 through 9, 6 and 7 wherein said species is selected from the group consisting of *Glomus mosseae, Glomus intraradices, Glomus vesiculiferum, Gigaspora gigantea, Gigaspora margarita, Entrophorspora colombiana* and *Scutellospora pellucida*.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:1:

GTCTAGTATA ATCGTTATAC AGG                                    2 3

( 2 ) INFORMATION FOR SEQ ID NO:2:

( i ) SEQUENCE CHARACTERISTICS:
( A ) LENGTH: 23 base pairs
( B ) TYPE: nucleic acid
( C ) STRANDEDNESS: single
( D ) TOPOLOGY: linear ( x i ) SEQUENCE DESCRIPTION: SEQ ID NO:2:

CCTGTATAAC GATTATACTA GAC                                    2 3

( 2 ) INFORMATION FOR SEQ ID NO:3:

( i ) SEQUENCE CHARACTERISTICS:
   ( A ) LENGTH: 439 base pairs
   ( B ) TYPE: nucleic acid
   ( C ) STRANDEDNESS: double
   ( D ) TOPOLOGY: linear ( x i ) SEQUENCE DESCRIPTION: SEQ ID NO:3:

| | | | | | |
|---|---|---|---|---|---|
| TTATAATTTA | TTTGATAGTA | CCTTACTACT | TGGATAACCG | TGGTTCTAGA | GCTAATACAT | 60 |
| GCTAAAAGCC | TCCGACTTCT | GGAAGGGGGT | GTATTTATTA | GATAAAAAAC | CAATATCGGG | 120 |
| CAACCGATTC | CCTTGGTGAT | TCATAATAAC | TTTTCGAATC | GTAGCTTTAC | GTCGACGATG | 180 |
| AATCATTCAA | ATTTCTGCCC | TATCAACTTT | CGATGGTAGG | ATAGAGGCCT | ACCATGGTGG | 240 |
| TAACGGGTAA | CGGGGTGTTA | GGGCACGACA | CCGGAGAGGG | AGCCTGAGAA | ACGGCTACCA | 300 |
| CATCCAAGGA | TGGCAGCAGG | CGCGCAAATT | ACCCAATCCC | GACACGGGGA | GGTAGTACAA | 360 |
| TAAATAACAA | TACGGGGTTC | TTTAGGATCT | CGTAGGAATG | AGTACAATTT | AAATCTCTTA | 420 |
| ACGAGGAACA | ATTGGAGGG | | | | | 439 |

( 2 ) INFORMATION FOR SEQ ID NO:4:

( i ) SEQUENCE CHARACTERISTICS:
   ( A ) LENGTH: 446 base pairs
   ( B ) TYPE: nucleic acid
   ( C ) STRANDEDNESS: double
   ( D ) TOPOLOGY: linear ( x i ) SEQUENCE DESCRIPTION: SEQ ID NO:4:

| | | | | | |
|---|---|---|---|---|---|
| TTATAATTTA | TTTGATAGTA | CCTTACTACT | TGGATAACCG | TGGTAATTCT | AGAGCTAATA | 60 |
| CATGCTAAAA | CCTCCGACTT | CTGGAAGGGG | GTGTATTTAT | TAGATAAAAA | ACCAATATCG | 120 |
| GGCAACCGAT | TCCCTTGGTG | ATTCATAATA | ACTTTTCGAA | TCGTATGACT | TTACGTCGAC | 180 |
| GATGAATCAT | TCAAATTTCT | GCCCTATCAA | CTTTCGATGG | TAGGATAGAG | GCCTACCATG | 240 |
| GTGGTAACGG | GTAACGGGGT | GTTAGGGCAC | GACACCGGAG | AGGGAGCCTG | AGAAACGGCT | 300 |
| ACCACATCCA | AGGATGGCAG | CAGGCGCGCA | AATTACCCAA | TCCGACACGG | GGAGGTAGTG | 360 |
| ACAATAAATA | ACAATACGGG | GTTCTTTAGG | ATCTCGTAAT | GGAATGAGT | ACAATTTAAA | 420 |
| TCTCTTAACG | AGGAACAATT | GGAGGG | | | | 446 |

( 2 ) INFORMATION FOR SEQ ID NO:5:

( i ) SEQUENCE CHARACTERISTICS:
   ( A ) LENGTH: 444 base pairs
   ( B ) TYPE: nucleic acid
   ( C ) STRANDEDNESS: double
   ( D ) TOPOLOGY: linear ( x i ) SEQUENCE DESCRIPTION: SEQ ID NO:5:

| | | | | | |
|---|---|---|---|---|---|
| TTATAGTTTA | TTTGATAGTA | CAATTACTAC | TTGGATAACC | GTGGTAATTC | TAGAGCTAAT | 60 |
| ACATGCTAAA | AATCCCGACT | TCTGGAAGGG | ATGTATTTAT | TAGATAAAAA | CCAATAACCT | 120 |
| TCGGGTTTCC | CTTGGTGATT | CATGATAACT | TTTCGAATCG | TATGGCCTTG | TGCTGACGAT | 180 |
| GTATCATTCA | AATTTCTGCC | CTATCAACTT | TCGATGGTAG | GATAGAGGCC | TACCATGGTT | 240 |
| TTAACGGGTA | ACGGGGAATT | AGGGTTCGAT | TCCGGAGAGG | GAGCCTGAGA | ACGGCTACC | 300 |
| ACATCCAAGG | AAGGCAGCAG | GCGCGCAAAT | TACCCAATTC | CGATACGGGG | AGGTAGTGAC | 360 |
| AATAAATAAC | AATACAGGGC | TCTTATGGGT | CTTGTAATTG | GAATGAGTAC | AATTTAAATC | 420 |
| TCTTAACGAG | GAACAATTGG | AGGG | | | | 444 |

( 2 ) INFORMATION FOR SEQ ID NO:6:

( i ) SEQUENCE CHARACTERISTICS:
    ( A ) LENGTH: 444 base pairs
    ( B ) TYPE: nucleic acid
    ( C ) STRANDEDNESS: double
    ( D ) TOPOLOGY: linear ( x i ) SEQUENCE DESCRIPTION: SEQ ID NO:6:

| | | | | | |
|---|---|---|---|---|---|
| TTATAGTTTA | TTTGATAATA | CCTTTACTAC | TTGGATAACC | GTGGTAATTC | TAGAGCTAAT | 60 |
| ACATGCTAAA | AATCCCGACT | TCTGGAAGGG | ATGTATTTAT | TAGATAAAAA | ACCAACGTGG | 120 |
| GCAACCACTC | ATCTGGTGAT | TCATAATAAC | TTTTCGAATC | GTATGGCCTA | GTGCCGACGA | 180 |
| TGATTCATTC | AAATTTCTGC | CCTATCAACT | TTCGATGGTA | GGATAGAGGC | CTACCATGGT | 240 |
| ATTTACGGGT | AACGGGGAAT | TAGGGTTCGA | TTCCGGAGAG | GGAGCCTGAG | AAACGGCTAC | 300 |
| CACATCCAAG | GAAGGCAGCA | GGCGCGCAAA | TTACCCAATC | CGATACGGGG | AGGTAGTGAC | 360 |
| AATAAATAAC | AATACAGGGC | CTTTTGGGT | CTTGTAATTG | GAATGAGTAC | AATTTAAATC | 420 |
| CCTTAACGAG | GAACAATTGG | AGGG | | | | 444 |

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

GTCGACTCCT GCCAGTAGTC ATATGCTT                              28

( 2 ) INFORMATION FOR SEQ ID NO:8:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

GTAGTCATAT GCTTGTCTC                                        19

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

GGCTGCTGGC ACCAGACTTG C                                    21

( 2 ) INFORMATION FOR SEQ ID NO:10:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

AATATACGCT ATTGGAGCTG G                                    21

( 2 ) INFORMATION FOR SEQ ID NO:11:

( i ) SEQUENCE CHARACTERISTICS:
        ( A ) LENGTH: 21 base pairs
        ( B ) TYPE: nucleic acid ( C ) STRANDEDNESS: single
( D ) TOPOLOGY: linear ( x i ) SEQUENCE DESCRIPTION: SEQ ID NO:11:

GCAAGTCTGG TGCCAGCAGC C 21

( 2 ) INFORMATION FOR SEQ ID NO:12:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:12:

TTGGAGGGCA AGTCTGGTGC C 21

( 2 ) INFORMATION FOR SEQ ID NO:13:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:13:

CTTCCGTCAA TTCCTTTAAG 20

( 2 ) INFORMATION FOR SEQ ID NO:14:

( i ) SEQUENCE CHARACTERISTICS:
( A ) LENGTH: 19 base pairs
( B ) TYPE: nucleic acid
( C ) STRANDEDNESS: single
( D ) TOPOLOGY: linear ( x i ) SEQUENCE DESCRIPTION: SEQ ID NO:14:

CCCGTGTTGA GTCAAATTA 19

( 2 ) INFORMATION FOR SEQ ID NO:15:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:15:

AACTTAAAGG AATTGACGGA AG 22

( 2 ) INFORMATION FOR SEQ ID NO:16:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:16:

GGGGGAGTAT GGTCGCAAGG C 21

( 2 ) INFORMATION FOR SEQ ID NO:17:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:17:

GCATCACAGA CCTGTTATTG CCTC                                            24

(2) INFORMATION FOR SEQ ID NO:18:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:18:

CAGTGTAGCG CGCGTGCGGC                                                 20

(2) INFORMATION FOR SEQ ID NO:19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:19:

GAGGCAATAA CTGGTCTGTG ATGC                                            24

(2) INFORMATION FOR SEQ ID NO:20:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:20:

TCCGCAGGTT CACCTACGGA                                                 20

(2) INFORMATION FOR SEQ ID NO:21:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (xi) SEQUENCE DESCRIPTION: SEQ ID NO:21:

GCGGCCGCTA CGGACCTTGT TACGACTT                                        28